(12) United States Patent
Tsonton et al.

(10) Patent No.: US 8,485,964 B2
(45) Date of Patent: Jul. 16, 2013

(54) GASTRIC BAND WITH SUPPLY TUBE CHECK VALVE

(75) Inventors: Mark Tsonton, Union Township, OH (US); Daniel J. Mumaw, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1236 days.

(21) Appl. No.: 11/798,632

(22) Filed: May 15, 2007

(65) Prior Publication Data

US 2008/0287969 A1    Nov. 20, 2008

(51) Int. Cl.
*A61F 2/00* (2006.01)

(52) U.S. Cl.
USPC ............................... 600/37; 600/31; 604/909

(58) Field of Classification Search
USPC ........................... 600/29–32, 37; 128/DIG. 25
See application file for complete search history.

(56) References Cited

U.S. PATENT DOCUMENTS

| 4,256,093 | A | * | 3/1981 | Helms et al. | 600/31 |
| 4,584,990 | A | * | 4/1986 | Haber et al. | 600/31 |
| 4,634,443 | A | * | 1/1987 | Haber | 600/31 |
| 5,259,399 | A | | 11/1993 | Brown | |
| 2004/0254625 | A1 | * | 12/2004 | Stephens et al. | 623/1.1 |

FOREIGN PATENT DOCUMENTS

| EP | 0119596 | 9/1984 |
| EP | 0283539 | 9/1988 |
| EP | 1520564 | 4/2005 |
| JP | 2003-236446 | 8/2003 |
| JP | 2005-342520 | 12/2005 |
| WO | WO 02/19953 | 3/2002 |

* cited by examiner

*Primary Examiner* — Charles A Marmor, II
*Assistant Examiner* — Carrie R Dorna

(57) ABSTRACT

A balloon-type gastric band includes a balloon shaped and dimensioned to circumscribe the stomach at a predetermined location. The balloon includes a longitudinally extending body. A supply tube is secured to the balloon for fluid communication with an internal cavity of the balloon, wherein the supply tube includes a valve controlling the flow of fluid to and from the balloon.

10 Claims, 3 Drawing Sheets

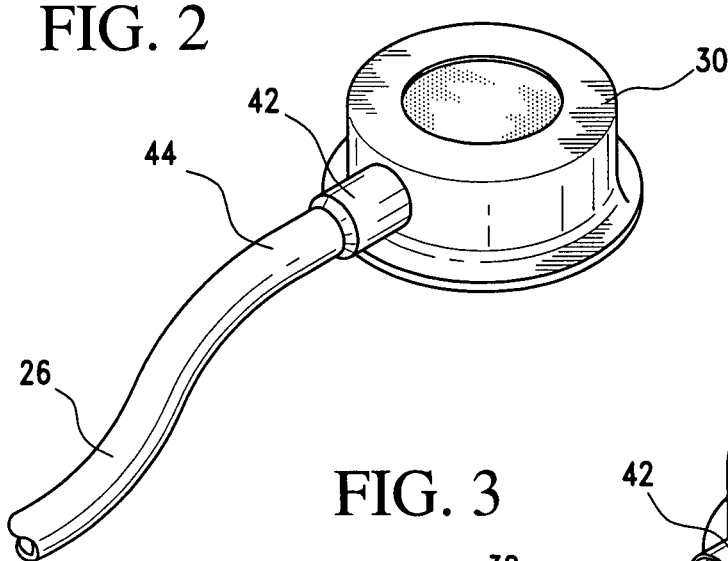
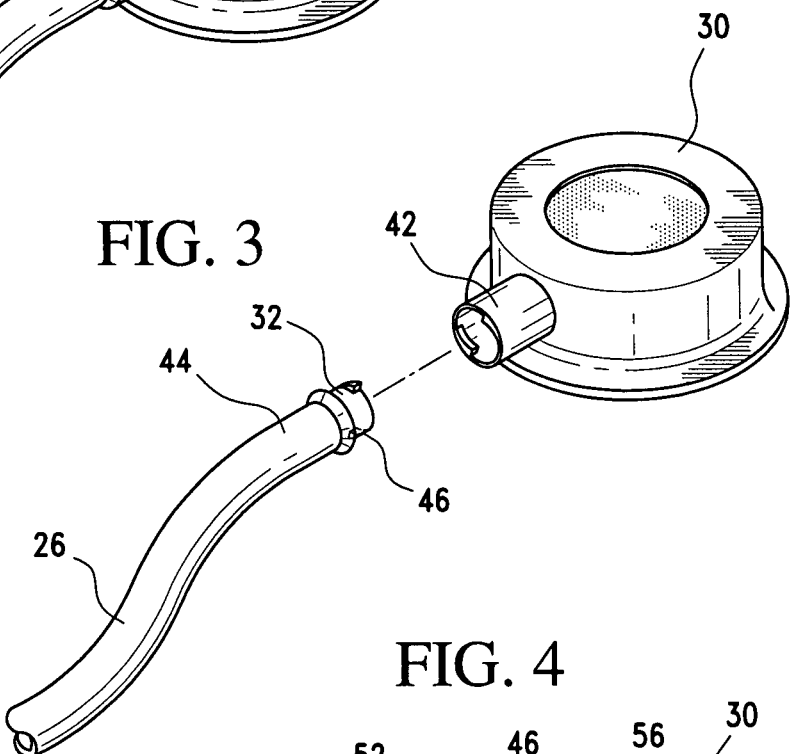
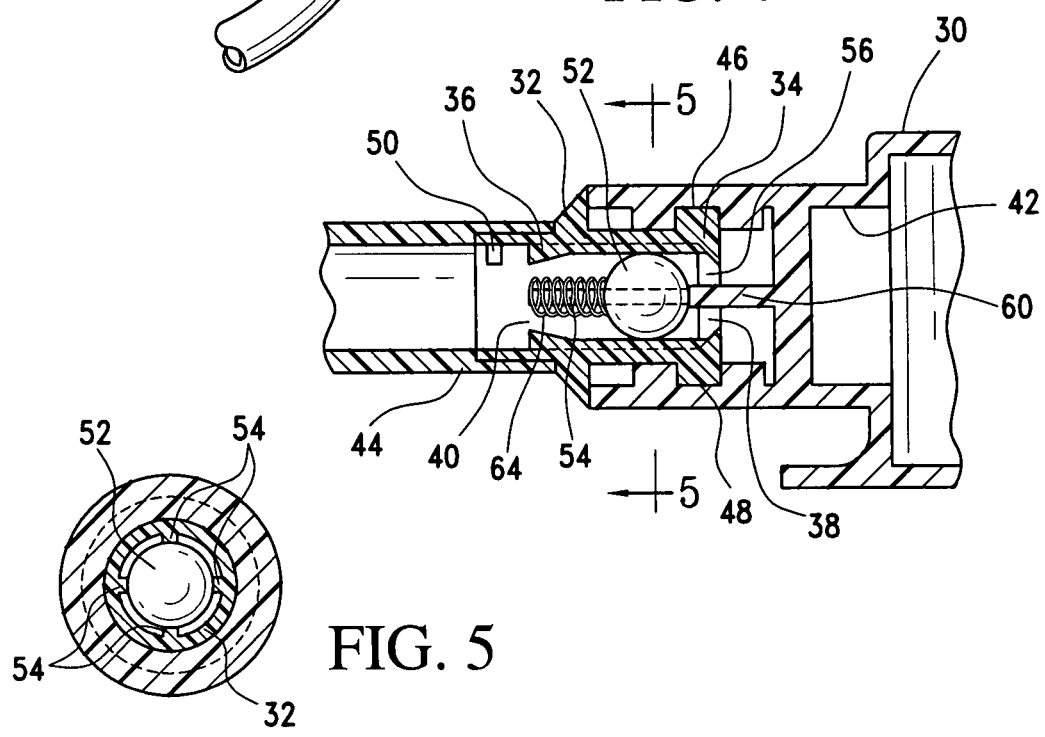

GASTRIC BAND WITH SUPPLY TUBE CHECK VALVE

BACKGROUND OF THE INVENTION

1. Field of the Invention

The invention relates to a gastric band and related accessories. More specifically, the invention relates to a supply tube check valve for use with a gastric band.

2. Description of the Related Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of one hundred billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastroplastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is one of these methods. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980's, gastric bands have provided an effective alternative to gastric bypass and other irreversible surgical weight loss treatments for the morbidly obese. Several alternate procedures are performed under the heading of gastric-banding. Some banding techniques employ a gastric ring, others use a band, some use stomach staples and still other procedures use a combination of rings, bands and staples. Among the procedures most commonly performed are vertical banded gastroplasty (VBG), silastic ring gastroplasty (SRG) and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages overeating.

In practice, the gastric band is inserted behind the stomach and the ends of the gastric band are coupled to latch the device about the stomach. However, when balloon-type gastric bands are used, the balloon must be inflated to ensure proper constriction of the stomach. This is commonly achieved by coupling the balloon to a fluid injection port, for example, a velocity port as is commonly employed within the industry. However, the attachment of the balloon, supply tube and fluid source can sometimes be complicated. In particular, in current low pressure gastric band products, prior to inserting the gastric band into the body the surgeon has to evacuate the gastric band and tie a knot in the supply tube to maintain evacuation of the gastric band during the procedure. After the procedure is complete, the surgeon cuts the knot off of the supply tube. A locking connector is slid onto the supply tube and then the supply tube is pushed onto the barbed fitting on the fluid injection port. The locking connector is then slid up and locked to the fluid injection port to prevent the supply tube and fluid injection port from coming disconnected in the body postoperatively. As those skilled in the art will certainly appreciate, this is a difficult procedure and a need, therefore, exists for improvements in the manner in which a balloon-type gastric band is applied to the stomach and secured to a fluid injection port. The present invention provides a mechanism for overcoming these difficulties.

SUMMARY OF THE INVENTION

It is, therefore, an object of the present invention to provide a balloon-type gastric band. The gastric band includes a balloon shaped and dimensioned to circumscribe the stomach at a predetermined location. The balloon includes a longitudinally extending body. A supply tube is secured to the balloon for fluid communication with an internal cavity of the balloon, wherein the supply tube includes a valve controlling the flow of fluid to and from the balloon.

It is also another object of the present invention to provide a gastric band wherein the valve is a check valve.

It is also an object of the present invention to provide a gastric band wherein the check valve is a ball check valve.

It is a further object of the present invention to provide a gastric band wherein the ball check valve is spring biased.

It is still another object of the present invention to provide a gastric band including a fluid injection port shaped and dimensioned for selective attachment to the balloon for fluid communication therewith.

It is yet a further object of the present invention to provide a gastric band wherein the valve may be removed from the supply tube prior to attachment of the supply tube to the fluid injection port.

It is also another object of the present invention to provide a gastric band wherein the fluid injection port is shaped and dimensioned for selective attachment to the valve.

It is also an object of the present invention to provide a gastric band wherein the fluid injection port includes a central barb selectively engaging the valve for opening the check valve for the flow of fluid from the fluid injection port to the balloon.

It is also another object of the present invention to provide a gastric band wherein the valve is spring biased.

It is a further object of the present invention to provide a gastric band wherein the valve is a spring biased, ball check valve and the central barb selectively engages the ball to open the valve for the flow of fluid from the fluid injection port to the balloon.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a perspective view of the distal end of the supply tube secured to a fluid injection port.

FIG. 3 is a perspective view of the distal end of the supply tube detached from the fluid injection port.

FIGS. 4 and 5 are cross sectional views of the supply tube/fluid injection port in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Figure 1:
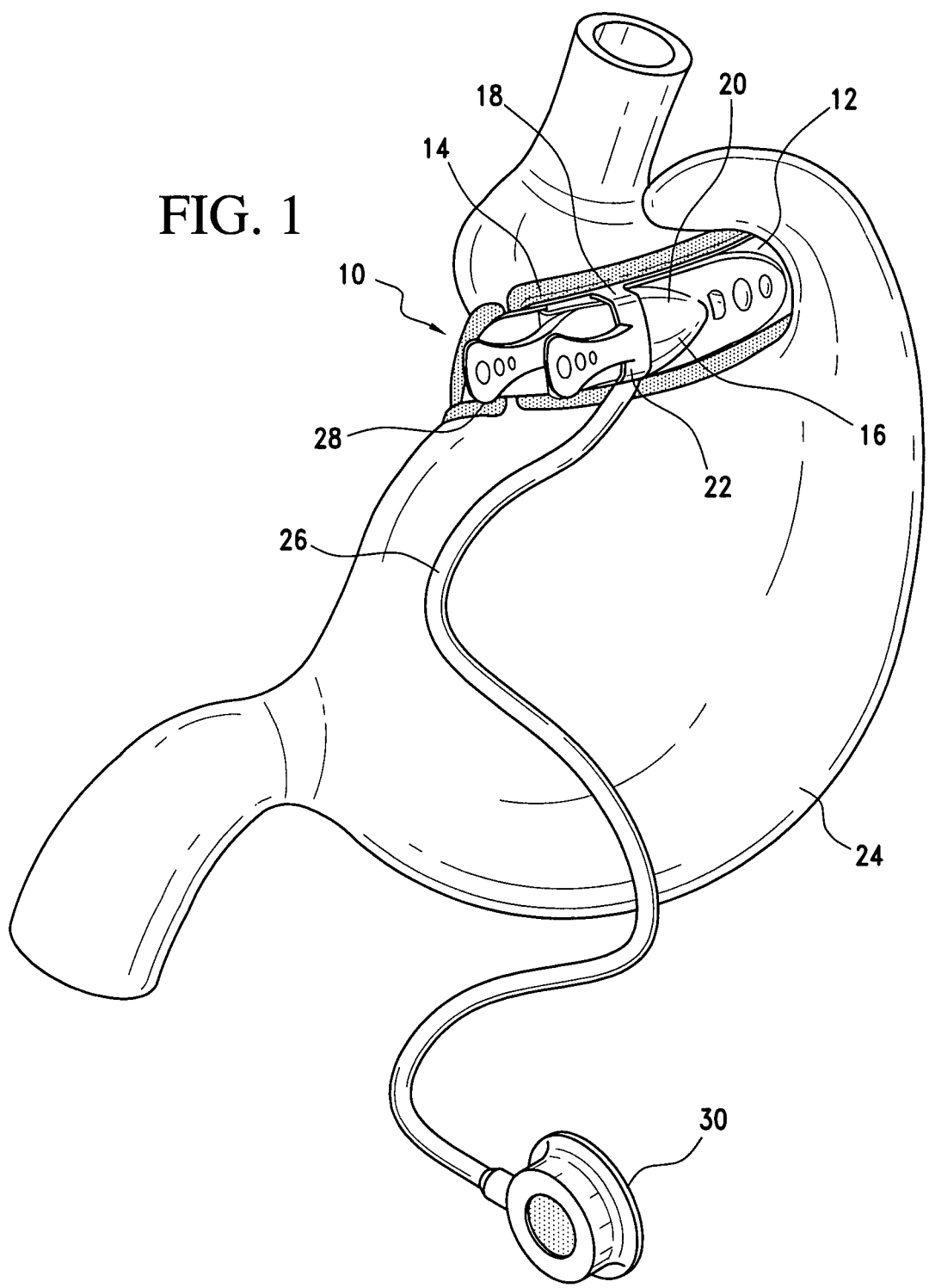
FIG. 1 is a perspective view of a balloon-type gastric band in accordance with the present invention secured about a patient's stomach.
Figure 6:
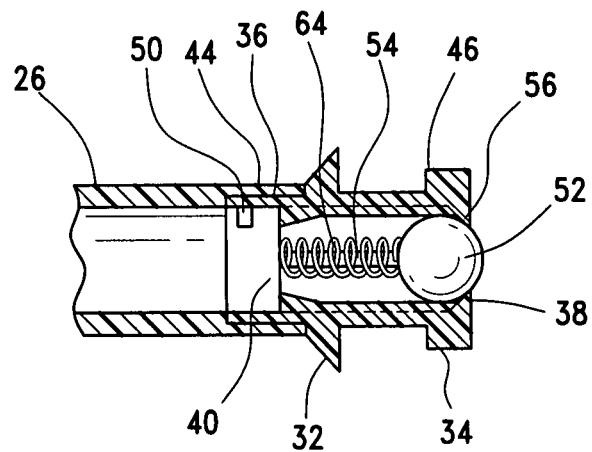
FIG. 6 is a cross sectional view of the supply tube unsecured to the fluid injection port.
Figure 7:
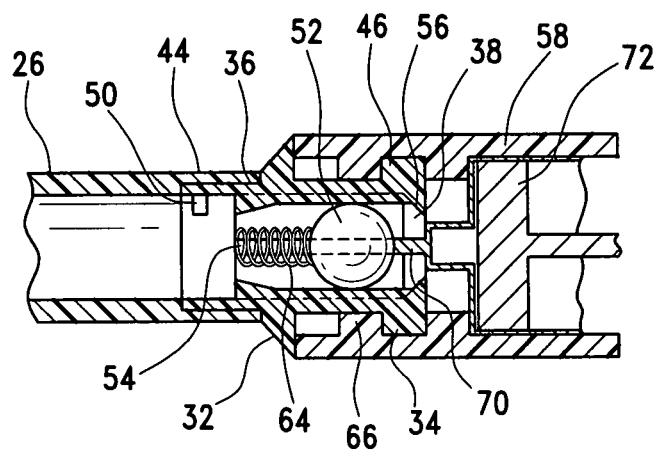
FIG. 7 is a cross sectional view of the supply tube secured to a syringe used in evacuating the balloon of the gastric band.

Referring to FIGS. 1 through 7, a balloon-type gastric band 10 is disclosed in accordance with a preferred embodiment of the present invention. The gastric band 10 is generally composed of a reinforcing belt 12 to which an elongated balloon 14 is secured. The belt 12 includes a first end 16 and a second end 18 to which first and second latching members 20, 22 are respectively secured when attached about a patient's stomach 24. In accordance with a preferred embodiment the first and second latching members 20, 22 are shaped and dimensioned for selective engagement, and are the same as disclosed in commonly owned U.S. patent application Ser. No. 11/182,072, entitled "Latching Device for Gastric Band", filed Jul. 15, 2005, which is incorporated herein by reference.

In accordance with a preferred embodiment, the belt 12 and balloon 14 are constructed as disclosed in commonly owned U.S. patent application Ser. No. 11/364,343, filed Mar. 1, 2006, entitled "Precurved Gastric Band", which is incorporated herein by reference. In general, the belt 12 and balloon 14 may be respectively coupled by either overmolding or separate molding with subsequent adhesive bonding. In accordance with preferred embodiments, and as those skilled in the art will certainly appreciate, the balloon 14 and belt 12 may be secured together by either adhesive bonding, comolding, overmolding or mechanical connection (for example, coupling sleeves), which secures the balloon 14 and belt 12 in a manner resulting in the coupling of these distinct gastric band components.

With the foregoing in mind, the balloon 14 employed in accordance with a preferred embodiment of the present application is constructed of an elastomeric material. Due to the design of this balloon 14, it does not inflate or expand in a manner causing high strain in the balloon 14 when filled during gastric band adjustment. Rather, the balloon 14 is adapted to receive a large volume of fluid under a relatively low pressure. In this way, the balloon 14 receives fluid during application, but does not inflate or expand in a traditional manner creating strain along the walls of the balloon 14. In other words, when the balloon 14 is filled up to the volume recommended to achieve maximum stomach restriction, there is no expansion of the balloon material. Instead, the balloon 14 fills to some percentage of its total theoretical volume (that is, maximum fill volume). Since the balloon 14 is not filled even close to its maximum fill volume, it remains low pressure, allowing the balloon 14 to conform to the stomach rather than the stomach to a rigid balloon.

In accordance with a preferred embodiment of the present invention, the balloon 14 is designed with a maximum capacity of between approximately 10 cc and approximately 18 cc, and preferably 12 cc, although it will be fully filled for functioning in accordance with the present invention to achieve the smallest stoma size with approximately 9 cc to approximately 12 cc, and preferably 11 cc. By providing a balloon 14, which is not at its capacity when properly filled for functioning, the softness and conformance of the balloon 14 is improved. While specific volumes are disclosed in accordance with a preferred embodiment of the present invention, those skilled in the art will appreciate the filling volumes may be varied without departing from the spirit of the present invention.

As those skilled in the art will certainly appreciate, a supply tube 26 is used to connect the internal cavity 28 of the balloon 14 of the gastric band 10 with a fluid injection port 30, for example, a velocity port. The utilization of the supply tube 26 with a remote fluid injection port 30 allows for controlled inflation and deflation of the balloon 14 in a predetermined manner. The exact position of the supply tube 26 is important in that the surgeon does not want tubing to be a visual obstruction during locking and/or other manipulation of the gastric band 10. In addition, once placement of the gastric band 10 is complete, the supply tube 26 should not cause irritation to surrounding tissue (for example, sticking directly into the liver or spleen). Surgeons also do not want to pull the supply tube 26 through a retro-gastric tunnel, since they cannot easily see if the tissue is being damaged. The supply tube 26 should also be able to act as a safe grasping location for manipulation of the gastric band 10, the supply tube 26 must not kink at the junction to the gastric band 10 and prevent fluid flow, and the supply tube location should facilitate passage of the gastric band 10 through a small trocar. In accordance with a preferred embodiment, the supply tube 26 is connected to the balloon 14 as disclosed in commonly owned U.S. patent application Ser. No. 11/364,362, filed Mar. 1, 2006, entitled "Gastric Band", which is incorporated herein by reference.

As mentioned above, current low pressure gastric band products, prior to insertion into the body, require that the surgeon evacuate the gastric band and tie a knot in the supply tube to maintain evacuation of the gastric band during the procedure. After the procedure is complete, the surgeon cuts the knot off of the supply tube. A locking connector is slid onto the supply tube and then the supply tube is pushed onto the barbed fitting on the fluid injection port. The locking connector is then slid up and locked to the fluid injection port to prevent the supply tube and fluid injection port from becoming disconnected in the body postoperatively.

The need for knotting and cutting is obviated in accordance with the present invention by incorporating a check valve 32 at the end 62 of the supply tube 26. Then, instead of having to tie a knot in the end of the supply tube 26, the surgeon only needs to attach a syringe 58 and evacuate the gastric band 10 via the check valve 32. The check valve 32 helps the gastric band 10 maintain evacuation throughout the procedure.

More particularly, and with reference to FIGS. 2 to 7, the gastric band 10 includes a check valve 32 integrally formed at the proximal end 44 of the supply tube 26. The locking connector 46, in accordance with a preferred embodiment, is a male Luer lock, which is integrated with the check valve 32 for attachment to the fluid injection port 30 in a manner discussed below in greater detail. In practice, the surgeon may, therefore, evacuate the gastric band 10 with a syringe 58 and the check valve 32 ensures that evacuation is maintained throughout the procedure. Once the primary procedure is complete, the surgeon uses the locking connector 46 at the first end (or mating end) 34 of the check valve 32 to lock onto the fluid injection port 30. This function requires the fluid injection port 30 to have the same geometry as the syringe 58 so the male Luer lock, that is, the locking connector 46, on the check valve 32 is compatible with both the syringe 58 and the fluid injection port 30. In addition, and with reference to FIG. 4, the fluid injection port 30 is provided with a barb 60, which, when the check valve 32 is locked in place on the fluid injection port 30, keeps the check valve 32 open and allows the fluid to flow freely (in both directions) to and from the fluid injection port 30. This ensures that during a postoperative gastric band adjustment, the supply tube 26 patency is ensured.

More particularly, and with reference to FIGS. 4 and 5 where the gastric band 10 is shown connected to the fluid injection port 30 via the supply tube 26, the supply tube 26 is connected to the fluid injection port 30 that provides a controlled supply of fluid to the balloon 14 of the gastric band 10. Improved filling is achieved by incorporating the check valve 32 between the supply tube 26 and the fluid injection port 30. In accordance with a preferred embodiment, the check valve 32 includes a first end 34 and second end 36. The first end 34 of the check valve 32 includes the input end 38 and the second end 36 of the check valve 32 includes the output end 40 (as referenced based upon the flow of fluid from the fluid injection port 30 to the balloon 14). The first end 34 is adapted for connection with the outlet 42 of the fluid injection port 30 and the second end 36 is adapted for connection with a proximal end 44 of the supply tube 26.

The check valve 32 is constructed to prevent the flow of fluid therethrough in the direction from the first end 34 to the second end 36 to prevent the flow of fluid to the gastric band 10 while it is being evacuated before the supply tube 26 is secured to the pressurized fluid injection port 30, while permitting the flow of fluid from the second end 36 to the first end 34 in a manner which allows for the evacuation of a gastric band 10 attached thereto. Ultimately, the check valve 32 is structured to prevent the flow of fluid into the balloon 14 while the gastric band 10 is being secured about the stomach and the supply tube 26 has yet to be secured to the fluid injection port 30.

However, and as discussed above, once the balloon 14 of the gastric band 10 is evacuated, the proximal end 44 of the supply tube 26, in particular, the first end 34 of the check valve 32, is coupled to fluid injection port 30 and the balloon 14 is ready for inflation. In order to provide for the flow of fluid from the fluid injection port 30 through the check valve 32 and to the balloon 14, the check valve 32 must be opened. A central barb 60 is, therefore, provided at the outlet 42 of the fluid injection port 30. The barb 60 is shaped and dimensioned to engage the check valve 32 and open it in a manner permitting the flow of fluid from the fluid injection port 30 to the balloon 14.

The check valve 32 of the present invention may employ a variety of known valve structures. It is contemplated the valve structure may be a ball check valve, a butterfly valve, gate valve, vacuum relief valve, etc., although other known valve structures could certainly be implemented without departing from the spirit of the present invention. As shown in FIGS. 4, 5, 6 and 7, the check valve 32 is a ball type check valve and, therefore, includes a central ball 52 which is guided along a plurality of rails 54 between the first end 34 of the check valve 32 and the second end 36 of the check valve 32. The ball 52 is biased toward the first end 34 by a spring 64. When fully biased toward the first end 34, the ball 52 engages the valve seat 56 in a manner preventing the flow of fluid from the first end 34 toward the second end 36. When the ball 52 is positioned away from the valve seat 56 due to the central barb 60 or the needle 70 of the syringe 58 pushing the ball 52 in a direction toward the second end 36 of the check valve, the rails 54 permit fluid to flow about the central ball 52 as it is forced from the fluid injection port 30 to the supply tube 26 with the central ball 52 supported by the rails 54 moved toward the second end 36 of the check valve 32 or as the fluid is drawn from the balloon 14 by the action of the syringe 58 in evacuating the balloon 14. While a preferred check valve structure has been disclosed herein, those skilled in the art will appreciate a variety of structures may be employed without departing form the spirit of the present invention.

In accordance with a preferred embodiment of the present invention, the first end 34 of the check valve 32 is provided with a male Luer lock 46 shaped and dimensioned for selective connection with a female Luer lock 48 formed at the outlet 42 of the fluid injection port 30. Although a Luer lock construction is disclosed in accordance with a preferred embodiment of the present invention, those skilled in the art will appreciate other connection structures may be employed without departing from the spirit of the present invention. Similarly, the syringe 58 is provided with a female Luer lock 66 for attachment during the evacuation stage.

With regard to the second end 36 of the check valve 32, it is provided with a barbed projection (not shown) shaped and dimensioned for frictional engagement within the proximal end 44 of the supply tube 26 leading to the internal cavity 28 of the balloon 14. As with the first end 34 of the check valve 32, a variety of connection structures are known to those skilled in the art and various connection structures may be applied in connecting the proximal end of the supply tube to the second end of the check valve without departing from the spirit of the present invention.

By incorporating a check valve 32 as described above into the line feeding fluid to the balloon 14 of the gastric band 10, the balloon 14 may be readily evacuated without requiring the surgeon to clamp the supply tube 26 prior to attachment of the supply tube 26 to the fluid injection port 30. This improves efficiency and minimizes the steps that must be taken during a gastric band application procedure. In addition, the check valve 32 is provided with a pressure sensor 50 to measure the amount of pressure in the gastric band 10.

The present gastric band 10 is utilized in the following manner. First, the balloon 14 of the gastric band 10 is evacuated by securing a syringe 58 to the first end 34 of the check valve 32, with the needle 70 of the syringe 58 moving the ball 52 away from the valve seat 56 and toward the second end 36 of the check valve 52, and all of the fluid from the balloon 14 is drawn out of the balloon 14, through the check valve 32 and into the syringe 58 as plunger 72 is moved. Once the evacuation of the balloon is completed, the gastric band 10 is secured about the stomach of a patient in a traditional manner. Thereafter, the proximal end 44 of the supply tube 26, in particular, the first end 34 of the check valve 32, is secured to the fluid injection port 30. Upon attachment of the outlet 42 of the fluid injection port 30 to the first end 34 of the check valve 32, the central barb 60 engages the ball 52 to move it off of the valve seat 56 and toward the second end 36 of the check valve 32. In this position, fluid may freely flow from the fluid injection port 30 to the balloon 14 and through the check valve 32.

In accordance with an alternate embodiment, the check valve may be cut from the supply tube after evacuation of the fluid from the balloon such that the supply tube may be directly connected to the fluid injection port.

In accordance with various preferred embodiments of the present invention, different tube placements may be employed as disclosed in commonly owned U.S. patent application Ser. No. 11/364,362, entitled "Gastric Band", filed Mar. 1, 2006, which is incorporated herein by reference.

Although the present invention is described for use in conjunction with gastric bands, those skilled in the art will appreciate the above invention has equal applicability to other types of implantable bands. For example, bands are used for the treatment of fecal incontinence. One such band is described in U.S. Pat. No. 6,461,292. Bands can also be used to treat urinary incontinence. One such band is described in U.S. Patent Application Publication No. 2003/0105385. Bands can also be used to treat heartburn and/or acid reflux. One such band is described in U.S. Pat. No. 6,470,892. Bands can also be used to treat impotence. One such band is described in U.S. Patent Application Publication No. 2003/0114729.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A balloon-type gastric band, comprising:
   a balloon shaped and dimensioned to circumscribe the stomach at a predetermined location;
   the balloon includes a longitudinally extending body;
   a supply tube including a distal end and a proximal end, the distal end of the supply tube being secured to the balloon for fluid communication with an internal cavity of the balloon, wherein the proximal end of the supply tube includes a valve controlling the flow of fluid to and from the balloon, a locking connector integrated with the valve, wherein the locking connector is shaped and dimensioned for selective connection to a fluid injection port;
   wherein the valve is a check valve, and wherein the check valve is constructed to prevent the flow of fluid from the proximal end of the supply tube to the balloon at the distal end of the supply tube and permit the flow of fluid from the balloon at the distal end of the supply tube toward the proximal end of the supply tube.

2. The balloon-type gastric band according to claim 1, wherein the check valve is a ball check valve.

3. The balloon-type gastric band according to claim 2, wherein the ball check valve is spring biased.

4. A balloon-type gastric band comprising:
   a balloon shaped and dimensioned to circumscribe the stomach at a predetermined location;
   the balloon includes a longitudinally extending body;
   a supply tube including a distal end and a proximal end, the distal end of the supply tube being secured to the balloon for fluid communication with an internal cavity of the balloon, wherein the proximal end of the supply tube includes a valve controlling the flow of fluid to and from the balloon, a locking connector integrated with the valve, wherein the locking connector is shaped and dimensioned for selective connection to a fluid injection port; and
   a fluid injection port shaped and dimensioned for selective attachment to the balloon for fluid communication therewith, wherein the valve is constructed to prevent the flow of fluid from the proximal end of the supply tube to the balloon at the distal end of the supply tube and permit the flow of fluid from the balloon at the distal end of the supply tube toward the fluid injection port at the proximal end of the supply tube.

5. The balloon-type gastric band according to claim 4, wherein the valve may be removed from the supply tube prior to attachment of the supply tube to the fluid injection port.

6. The balloon-type gastric band according to claim 4, wherein the fluid injection port includes a central barb selectively engaging the valve for opening the valve for the flow of fluid from the fluid injection port to the balloon.

7. The balloon-type gastric band according to claim 6, wherein the valve is spring biased.

8. The balloon-type gastric band according to claim 6, wherein the valve is a spring biased, ball check valve and the central barb selectively engages the ball to open the valve for the flow of fluid from the fluid injection port to the balloon.

9. A balloon-type gastric band, comprising:
   a balloon shaped and dimensioned to circumscribe the stomach at a predetermined location;
   the balloon includes a longitudinally extending body;
   a supply tube including a distal end and a proximal end, the distal end of the supply tube being secured to the balloon for fluid communication with an internal cavity of the balloon, wherein the proximal end of the supply tube includes a valve controlling the flow of fluid to and from the balloon;
   a fluid injection port shaped and dimensioned for selective attachment to the balloon for fluid communication therewith, wherein the valve is constructed to prevent the flow of fluid from the fluid injection port at the proximal end of the supply tube to the balloon at the distal end of the supply tube and permit the flow of fluid from the balloon at the distal end of the supply tube toward the fluid injection port at the proximal end of the supply tube.

10. The balloon-type gastric band according to claim 9, wherein the fluid injection port includes a central barb selectively engaging the valve for opening the valve for the flow of fluid from the fluid injection port to the balloon.

* * * * *